US008053596B2

(12) United States Patent
Neigel et al.

(10) Patent No.: US 8,053,596 B2
(45) Date of Patent: Nov. 8, 2011

(54) PROCESS FOR PRODUCING ALXYL GLYCERYL SULFONATES

(75) Inventors: Dennis Neigel, Salisbury, NC (US); Michael Calhoun, Pompano Beach, FL (US); Ed Richman, Lower Gwynedd, PA (US)

(73) Assignee: Third Stream Bioscience, Inc., Ft. Lauderdale, FL (US)

( * ) Notice: Subject to any disclaimer, the term of this patent is extended or adjusted under 35 U.S.C. 154(b) by 115 days.

(21) Appl. No.: 12/610,833

(22) Filed: Nov. 2, 2009

(65) Prior Publication Data

US 2011/0105787 A1 May 5, 2011

(51) Int. Cl.
*C07C 309/10* (2006.01)

(52) U.S. Cl. ........................................ 562/110

(58) Field of Classification Search .................. 562/110
See application file for complete search history.

(56) References Cited

U.S. PATENT DOCUMENTS

| | | | |
|---|---|---|---|
| 2,989,547 | A | 6/1961 | Whyte |
| 3,024,273 | A | 3/1962 | Whyte et al. |
| 3,228,979 | A | 1/1966 | Gaertner |
| 5,310,508 | A | 5/1994 | Subramanyam et al. |
| 5,322,643 | A | 6/1994 | Schwartz et al. |
| 5,567,359 | A | 10/1996 | Cassidy et al. |
| 5,621,139 | A | 4/1997 | Silvis |
| 5,672,740 | A | 9/1997 | Subramanyam et al. |

FOREIGN PATENT DOCUMENTS

| | | |
|---|---|---|
| WO | WO 91/09924 A1 | 7/1991 |
| WO | WO 91/09931 A1 | 7/1991 |

*Primary Examiner* — Peter O Sullivan

(74) *Attorney, Agent, or Firm* — Brinks Hofer Gilson & Lione

(57) ABSTRACT

A process for preparing alkyl glyceryl sulfonate includes fractionally distilling an alkyl glyceryl epoxide mixture to afford alkyl glyceryl epoxide of formula IV:

IV

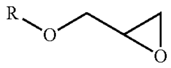

where R is a $C_{4-12}$ alkyl, in at least about 98.0% purity by weight with respect to epoxidized compounds, the epoxidized compounds comprising the alkyl glyceryl epoxide of formula IV, dimer alkyl glyceryl epoxide of formula V, and trimer alkyl glyceryl epoxide of formula VI:

V

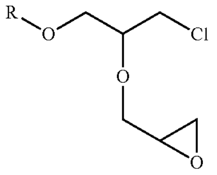

VI

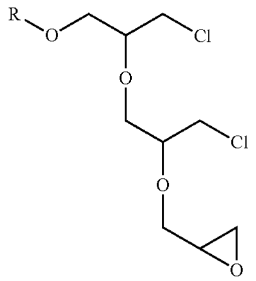

where R is a $C_{4-12}$ alkyl; and reacting the at least about 98.0% alkyl glyceryl epoxide of formula IV with a mixture of an alkali bisulfite and an alkali sulfite in a sulfonation reaction at a temperature, to afford the alkyl glyceryl sulfonate of formula I:

I

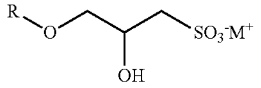

where R is a $C_{4-12}$ alkyl and M is an alkali metal.

28 Claims, No Drawings

PROCESS FOR PRODUCING ALXYL GLYCERYL SULFONATES

FIELD OF THE INVENTION

The present invention relates to synthesis methods for surfactants. More specifically, it relates to improved synthesis methods for alkyl glyceryl sulfonate (AGS) anionic surfactants. Such surfactants are particularly useful in combination with organic acids as topical antimicrobials.

BACKGROUND OF THE INVENTION

Human and mammalian health is certainly impacted by the spread of microbial entities at home, school, work and in the environment generally. Despite medical advances in infectious disease prevention and treatment, viruses and bacteria continue to cause a variety of sicknesses and ailments, prompting high absenteeism in schools and places of employment. In the wake of widespread food poisoning and the like, the public has become even further concerned with sanitization, both of person and property. Additionally, deadly antibiotic resistant bacteria like MRSA, formerly a nosocomial infection, is now primarily community acquired. Indeed, the World Health Organization continues to monitor avian flu out of concern for the potential of a serious global pandemic. A principal route for the spread of such infections is contact, either with an infected person (a handshake) or a contaminated object (a doorknob). Consequently, those of skill in the art have focused their research endeavors on the identification and deployment of more efficacious disinfectant and antiseptic compositions, and specifically those that provide both immediate and residual kill of microbes.

Antimicrobial compositions that exhibit rapid and residual kill of numerous bacteria and viruses have been disclosed in U.S. Patent Publication Nos. 2009/0035339, 2005/0271711, 2005/0260243, 2004/0001797, 2003/0235550, and in issued U.S. Pat. No. 7,569,530. Each of these disclosures is incorporated by reference herein. The compositions disclosed in these publications incorporate an organic acid or organic acid mixture and selected short-chain anionic surfactants. These compositions are adapted for direct application to human skin, without causing dryness or irritation. Moreover, they are designed for use with or without a water wash, and provide both immediate and residual effectiveness in either instance against a variety of viruses and bacteria.

A preferred family of anionic surfactants for these compositions are the alkyl glyceryl sulfonates, or $C_n$-AGS. They have been proven to be highly antimicrobial, yet are among the mildest of all anionic surfactants for human skin. One sodium alkyl glyceryl sulfonate is commercially available from the Proctor and Gamble Corporation, AGS-1214, CAS 68081-95-8. This anionic surfactant contains carbon chain lengths from $C_{10}$ to $C_{16}$, but is primarily $C_{12-14}$.

The general synthesis process for commercial AGS is well established. Examples of the synthesis can be found in U.S. Pat. Nos. 2,989,547 and 3,024,273. The synthesis involves a condensation reaction of a fatty alcohol with epichlorohydrin to afford an ether chlorohydrin which is then ring closed to the epoxide to produce an alkyl glyceryl epoxide (AGE). The epoxide is then treated with a mixture of sodium bisulfite and/or sodium sulfite in a sulfonation reaction to afford AGS.

Although this general process is commercially established, it has significant deficiencies when the resulting surfactant is contemplated as a drug substance for topical antimicrobials. Conventionally, a "heel" of AGS from a previous batch must be added to initiate the reaction and insure a uniform solution, which lowers the yield and creates a potential contamination problem. Additionally, the epoxidation reaction results in variable amounts of ether chlorohydrin monomer, dimer, and trimer. A typical monomer proportion is only 72-76%. These ratios carry over through sulfonation into AGS monomer, dimer, and trimer. Although U.S. Pat. No. 3,024,273 teaches that an increased dimer and trimer percentage leads to increased solubility and is preferred, it has been surprisingly discovered that increased monomer content and reduced dimer and trimer percentages provides increased antimicrobial effectiveness.

What is needed for industrial applications of AGS for antimicrobial compositions, is a process for the synthesis of AGS which minimizes dimer and trimer by-products, can be run in standard plant equipment such as stainless steel reactors, has high throughput, and minimizes cross-contamination among production batches.

SUMMARY OF THE INVENTION

The present invention removes disadvantages of the conventional process. AGE dimer and trimer are removed to a very high degree, producing a uniform AGE monomer feedstock with less than 1% dimer and undetectable trimer levels. It has further surprisingly been found that AGE monomer sulfonation, when performed under suitably controlled temperatures and pressures, is not corrosive to ordinary stainless steel reactor vessels at temperatures below 200° C. Thus, keeping the temperatures below 200° C. provides commercial advantages by allowing the process to be conducted in ordinary stainless steel vessels without corrosion, provided reaction conditions are suitably controlled to temperatures lower than the conventional process.

Additionally, controlled reactions at lower temperatures for longer durations produce a surprisingly high finished yield in excess of 95% without the inclusion of a "heel". High finished yield desirably minimizes unreacted residue. The present invention usefully results in a higher yield of a higher purity, uniformly monomeric AGS. This high purity monomer is preferred because it provides enhanced antimicrobial effectiveness.

Thus, one aspect of the invention relates to a process for preparing alkyl glyceryl sulfonate. This process includes fractionally distilling an alkyl glyceryl epoxide mixture to afford alkyl glyceryl epoxide of formula IV:

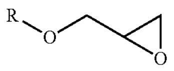

IV where R is a $C_{4-12}$ alkyl, in at least about 98.0% purity by weight with respect to epoxidized compounds. The epoxidized compounds include, but are not limited to the alkyl glyceryl epoxide of formula IV, dimer alkyl glyceryl epoxide of formula V, and trimer alkyl glyceryl epoxide of formula VI:

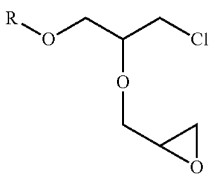

V

-continued

VI

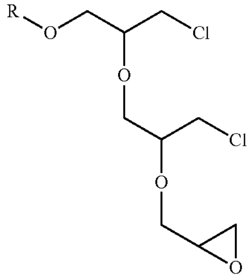

where R is a $C_{4-12}$ alkyl.

The process further includes reacting at least about 98.0% alkyl glyceryl epoxide of formula IV with a mixture of an alkali bisulfite and an alkali sulfite in a sulfonation reaction at a temperature to afford the alkyl glyceryl sulfonate of formula I:

I

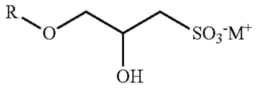

where R is a $C_{4-12}$ alkyl and M is an alkali metal.

The percentage of dimer alkyl glyceryl epoxide of formula V after the fractional distillation step may be at or below about 0.36% by weight.

The percentage of trimer alkyl glyceryl epoxide of formula VI after the fractional distillation step may be about zero by weight.

In one aspect of the invention, the alkyl glyceryl epoxide of formula IV may be reacted with alkali sulfite and alkali bisulfite in a stainless steel reactor. The stainless steel reactor may be passivated with an acid prior to the reacting step. In one example, the acid is nitric acid.

In one embodiment, the temperature of the sulfonation reaction may be below about 200° C. for a time between about 30 minutes to about 165 minutes, and the concentration of alkyl glyceryl epoxide of formula IV may be less than about 50.0% by weight. A concentration of alkyl glyceryl epoxide of formula IV less than about 50.0% by weight may produce up to about 95.9% yield of alkyl glyceryl sulfonate of formula I. The pH of the sulfonation reaction may be about 3 to about 6. The process may further include processing the alkyl glyceryl sulfonate of formula I into an antimicrobial composition.

In another embodiment, the temperature of the sulfonation reaction may about 185° C. to about 190° C., preferably about 190° C. The temperature may be held for a time between about 120 minutes to about 160 minutes. The sulfonation reaction may be performed at a concentration between about 30% to about 40% by weight alkyl glyceryl epoxide of formula IV.

The sulfonation reaction may afford less than about 0.5% by weight dimer alkyl glyceryl sulfonate of formula II:

II

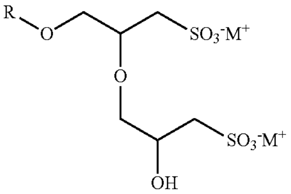

where R is a $C_{4-12}$ alkyl and M is an alkali metal.

Additionally, the sulfonation reaction may afford about zero percent by weight trimer alkyl glyceryl sulfonate of formula III:

III

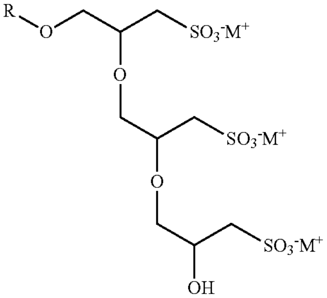

where R is a $C_{4-12}$ alkyl and M is an alkali metal.

In another aspect of the present invention, a process for preparing alkyl glyceryl sulfonate is disclosed. This process includes fractionally distilling an alkyl glyceryl epoxide mixture, to afford alkyl glyceryl epoxide of formula IV:

IV

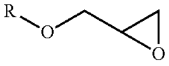

where R is a $C_{4-12}$ alkyl, in at least about 98.0% purity by weight with respect to epoxidized compounds, the epoxidized compounds comprising the alkyl glyceryl epoxide of formula IV, dimer alkyl glyceryl epoxide of formula V, and trimer alkyl glyceryl epoxide of formula VI:

V

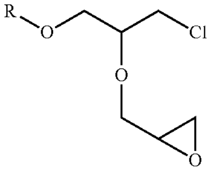

-continued

VI

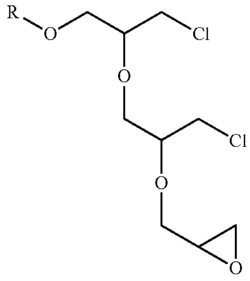

where R is a $C_{4-12}$ alkyl.

The process further includes reacting the at least about 98.0% alkyl glyceryl epoxide of formula IV with a mixture of an alkali bisulfite and an alkali sulfite in a sulfonation reaction at a pressure between about 115 PSIG and about 135 PSIG, at a concentration of about 15% to about 25% by weight, to afford the compound of formula I:

I

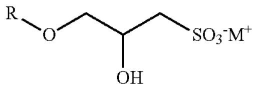

where R is a $C_{4-12}$ alkyl and M is an alkali metal.

These and other features, aspects, and advantages will become better understood with regard to the following detailed description and appended claims.

DETAILED DESCRIPTION OF THE INVENTION

When describing the compounds and processes of this invention, the following terms have the following meanings, unless otherwise indicated.

"Alkyl" refers to a hydrocarbon group which may be linear, cyclic, branched or a combination thereof having the number of carbon atoms designated (i.e., $C_{4-12}$ means four to twelve carbon atoms). Examples of alkyl groups include n-butyl, sec-butyl, t-butyl, cyclopropylmethyl, cyclopentyl, (cyclohexyl)methyl, etc.

"Alkali metal" refers to metals from Group 1 of the periodic table including lithium (Li), sodium (Na), potassium (K), rubidium (Rb), cesium (Cs), and francium (Fr); preferably lithium, sodium or potassium, and more preferably sodium.

The present invention provides an improved process for producing alkyl glyceryl sulfonates of formula I:

I

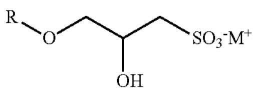

where R is $C_{4-12}$ alkyl, preferably $C_{6-10}$ alkyl, more preferably $C_8$ alkyl; and where M is an alkali metal, preferably Li, Na, or K, more preferably Na.

The process affords the compounds of formula I in up to about 95.9% yield and minimizes the presence of the dimer impurity of formula II to less than 0.5% and trimer impurity of formula III to undetectable levels:

II

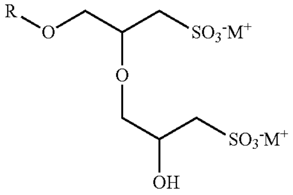

III

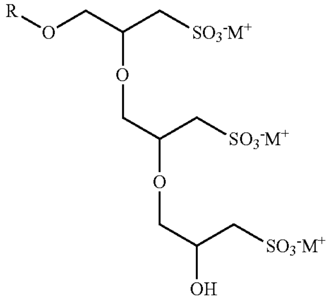

where R is $C_{4-12}$ alkyl; and each M is independently an alkali metal.

The process comprises fractionally distilling an AGE mixture to afford the AGE of formula (IV):

IV

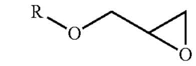

where R is $C_{4-12}$ alkyl.

The crude AGE prior to fractional distillation comprises the AGE of formula IV as the major component, and may comprise impurities such as the dimer epoxide of formula V and the trimer epoxide of formula VI:

V

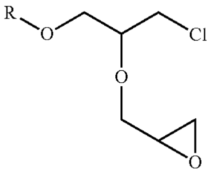

VI

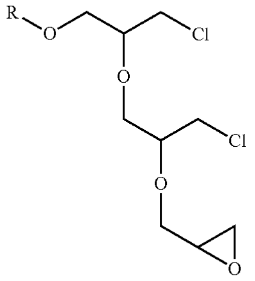

where R is $C_{4-12}$ alkyl. The fractional distillation affords the AGE of formula IV in at least about 98.0% purity by weight with respect to the epoxidized compounds. Epoxidized compounds include the AGE of formula IV and other epoxidized compounds including, but not limited to the dimer impurity of formula V and trimer impurity of formula VI.

In an embodiment of the invention, the crude AGE may be distilled in order to separate the preferred AGE monomer from dimer and trimer structures. Using 5 fractionation plates instead of 2 fractionation plates may reduce the dimer content by 0.34%, from 0.36% dimer to 0.02% dimer. Using 40 fractionation plates instead of 5 fractionation plates may reduce the dimer content by 0.012%, from 0.02% to 0.008% dimer. The monomer content, the content of the AGE of formula IV, may be increased by 0.8% by using 5 plates instead of 2 plates. In each of the 2, 5, or 40 plate examples, the amount of trimer was undetectable ("not detected" or "ND"). Thus, 2 to 5 plate columns are surprisingly efficient at yielding sufficiently pure AGE monomer.

With dimer and trimer sufficiently removed, it has further surprisingly been discovered that sulfonation may be accomplished in ordinary stainless steel vessels without corrosion provided reaction conditions are suitably controlled to temperatures lower than the conventional process. Prior to sulfonation, the stainless steel vessel may be passivated with an acid. Nitric acid is the preferred acid.

In one embodiment, the distilled AGE undergoes a sulfonation reaction in the presence of a mixture of an alkali bisulfite ($MHSO_3$) and alkali sulfite ($M_2SO_3$), where M is an alkali metal, to afford the alkyl glyceryl sulfonate. Preferably, the sulfonation is performed with a mixture of sodium sulfite and sodium bisulfate.

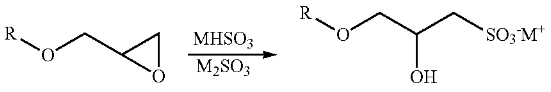

IV I

The sulfonation reaction is exothermic. The higher the concentration of AGE, the higher the natural peak temperature becomes. It has been found that in excess of 50% by weight of AGE, for example 60% AGE by weight in water, maximum peak temperatures exceed 210° C. If held at this temperature, the material will deteriorate into sludge. The final color of the reaction product may provide a visual indication of the success of the reaction, with darker colors providing evidence of vessel corrosion or metallic contamination of the product. Thus, translucently off-white AGS products are preferred. AGE concentrations below about 50% by weight are preferred.

In one embodiment, temperatures should remain below about 200° C., preferably in the range of 185-190° C., and most preferably about 190° C. Surprisingly, temperatures from about 184-190° C. can be reached naturally with AGE concentrations from about 30% to about 40% by weight. Therefore, in this preferable range of AGE concentration, no supplemental cooling is required to control temperature. Desirably, only standard supplemental vessel heating is required to maintain 190° C. for the desired length of time. Additionally, no heel of AGS product is required to initiate the reaction. The pH of the sulfonation reaction may be about 3 to about 6, preferably from about 4.8 to about 5.

The reaction time will vary depending on the reactive solids concentration. Lower concentrations of AGE by weight may require a longer duration than higher concentrations of AGE. In the preferred range, at 190° C., reaction yields at 60 minutes duration vary from 80.4% yield for 30% AGE by weight to 89.6% yield for 36.5% AGE by weight. Reaction yields for 40% and 50% of AGE by weight rise to 95.9% and 95.3%, respectively, when the temperature is maintained for 160 minutes. In light of these results, it is preferred to maintain the temperature for about 120 to 160 minutes.

Thus, in one embodiment, a preferable process that maximizes yield of finished AGS per batch is about 40% AGE by weight in water, rising naturally to a temperature of about 190° C. This temperature of about 190° C. is held for about 120 to about 160 minutes before being allowed to cool.

In another embodiment, it is desirable to run the sulfonation reaction at a lower pressure between about 115 PSIG and about 135 PSIG, such as about 130 PSIG. To achieve the reaction at a lower maximum pressure, the AGE concentration by weight may be reduced by adding water, thus reducing the maximum exothermic temperature. In one embodiment, the AGE concentration may be 20% by weight in water. This would result in a lower concentration of AGS product following reaction. For commercial production, it may be advantageous to decrease the concentration of AGS product in order to lower the freezing point of the solution for easier pumpability.

EXAMPLES

The following examples are offered to illustrate, but not to limit, the claimed invention.

Example 1

Fractional Distillation

AGE may be synthesized by methods known to one skilled in the art or procured conventionally. AGE was procured from Huntsman Chemical (The Woodlands, Tex.), whose C8-AGE is trade named Araldite DY-0. This AGE material comprised 76.9% monomer, 16.7% dimer, and 1.2% trimer. Distillation was performed using a standard benchtop vacuum fractionation distillation column and varying the number of plate equivalents to determine the best balance between desired material purity and process complexity.

The use of vacuum fractionation distillation on precursor AGE to remove dimer and trimer molecular structures typically yields the following results:

TABLE 1

| Fractional Distillation of AGE | | | |
|---|---|---|---|
| # Fractionation Plates | % monomer | % dimer | % trimer |
| 2 | 98.0 | 0.36 | ND |
| 5 | 98.0 | 0.02 | ND |
| 40 | 98.8 | 0.008 | ND |

Using 5 fractionation plates instead of 2 fractionation plates reduced the dimer content by 0.34%, from 0.36% dimer to 0.02% dimer. Using 40 fractionation plates instead of 5 fractionation plates reduced the dimer content by 0.012%, from 0.02% to 0.008% dimer. The monomer content was increased by 0.8% by using 40 plates instead of 5 plates. In each of the 2, 5, or 40 plate examples, the amount of trimer was undetectable (ND).

Example 2

Sulfonation Reaction

The sulfonation reaction was performed on a number of samples of AGE, at variable temperatures and reaction times, in a standard laboratory pressure vessel. The distilled AGE product was reacted with sodium sulfite and sodium bisulfate. The sulfonation reaction was accomplished in a stainless steel vessel. In sample numbers 5 and 11, the stainless steel autoclave vessel was passivated with nitric acid. In sample number 2, the stainless steel vessel was passivated with citric acid. Chemical characterization of the finished AGS was performed using high pressure liquid chromatography (HPLC), atomic absorption, gas chromatography, and gel penetration chromatography. These results are shown below:

TABLE 2

Sulfonation Reaction Examples

| Sample Number | AGE lot # | % monomer/ % dimer/ % tri | AGE % by weight | Reactor Passivation | Exo Max (° C.) | Reaction Time (Minutes) | % AGS | Final color |
|---|---|---|---|---|---|---|---|---|
| 1 | NC08-0508-3 | 96.9/0.356/0 | 23.2 | None | None | 30 | 85.4 | Blue |
| 2 | NC08-0508-1 | 98.0/0.197/0 | 27.5 | Citric Acid | 182 | 30 | 91.7 | Slight Gray |
| 3 | NC08-0508-1 | 98.0/0.197/0 | 28.7 | None | None | 30 | No Sample | Slight Yellow |
| 4 | NC08-0508-2&3 | 97.1/0.488/0 | 36.5 | None | 190 | 60 | 89.6 | Off-White |
| 5 | NC08-0514-3&4 | 98.8/0.008/0 | 30 | Nitric Acid | 184 | 60 | 80.4 | Off-White |
| 6 | NC08-0514-3&4 | 98.8/0.008/0 | 30 | None | 184 | 120 | 86.5 | Off-White |
| 7 | NC08-0522-3 | 98.0/0.019/0 | 40 | None | 189 | 163 | 95.9 | Off-White |
| 8 | NC08-0522-2&3 | 98.0/0.019/0 | 50 | None | 195 | 165 | 95.3 | Off-White |
| 9 | NC08-0522-3&4 | 98.0/0.019/0 | 60 | None | 210 | 161 | NR | Dark Brown |
| 10 | NC08-0522-4 | 98.0/0.019/0 | 40 | None | 184 | 120 | 90.3 | Slight Brown |
| 11 | NC08-0522-4&5 | 98.0/0.019/0 | 40 | Nitric Acid | 174 | 120 | 90.6 | Off-White |

As seen from Table 2, at range of about 184° C. to about 190° C., reaction yields at 60 minutes duration vary from 80.4% yield for 30% AGE by weight to 89.6% yield for 36.5% reactants by weight. Reaction yields for 40% and 50% AGE by weight rise to 95.9% and 95.3%, respectively, when the temperature is maintained for about 160 minutes.

Example 3

Sulfonation Reaction at a Reduced Pressure

In another embodiment, it is desirable to run the sulfonation reaction at a reduced pressure between about 115 PSIG and about 135 PSIG, such as 130 PSIG. To achieve the reaction at a lower pressure, the concentration of AGE by weight may be reduced by adding water. This results in a reduction of the maximum exothermic temperature. In one embodiment, the AGE may be 20% by weight in water.

It is intended that the foregoing detailed description be regarded as illustrative rather than limiting, and that it be understood that it is the following claims, including all equivalents, that are intended to define the spirit and scope of this invention.

We claim:

1. A process for preparing alkyl glyceryl sulfonate which comprises:

fractionally distilling an alkyl glyceryl epoxide mixture to afford alkyl glyceryl epoxide of formula IV:

IV

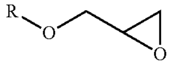

where R is a $C_{4-12}$ alkyl, in at least about 98.0% purity by weight with respect to epoxidized compounds, the epoxidized compounds comprising the alkyl glyceryl epoxide of formula IV, dimer alkyl glyceryl epoxide of formula V, and trimer alkyl glyceryl epoxide of formula VI:

V

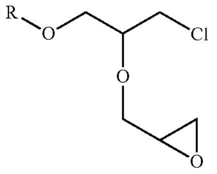

VI

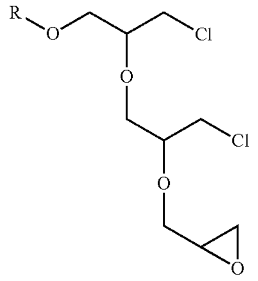

where R is a $C_{4-12}$ alkyl; and reacting the at least about 98.0% alkyl glyceryl epoxide of formula IV with a mixture of an alkali bisulfite and an alkali sulfite in a sulfonation reaction at a temperature to afford the alkyl glyceryl sulfonate of formula I:

I

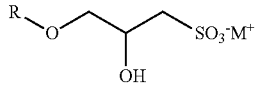

where R is a $C_{4-12}$ alkyl and M is an alkali metal.

2. The process of claim 1, where a percentage of the dimer alkyl glyceryl epoxide of formula V after the fractional distillation step is at or below about 0.36% by weight.

3. The process of claim 1, where the percentage of the trimer alkyl glyceryl epoxide of formula VI after the fractional distillation step is about zero by weight.

4. The process of claim 1, where reacting the at least about 98.0% alkyl glyceryl epoxide of formula IV with alkali sulfite and alkali bisulfite occurs in a stainless steel reactor.

5. The process of claim 4, where the stainless steel reactor is passivated with an acid prior to the reacting step.

6. The process of claim 5, where the acid is nitric acid.

7. The process of claim 1, where the temperature is about 185° C. to about 190° C.

8. The process of claim 7, where the temperature is about 190° C.

9. The process of claim 1, where the temperature is held for a time between about 120 minutes to about 160 minutes.

10. The process of claim 1, where the pH of the sulfonation reaction is about 3 to about 6.

11. The process of claim 1, where the sulfonation reaction is performed at a concentration of between about 30% to about 40% by weight alkyl glyceryl epoxide of formula IV.

12. The process of claim 1, where a concentration of alkyl glyceryl epoxide of formula IV of less than 50% by weight produces up to 95.9% yield of the alkyl glyceryl sulfonate of formula I.

13. The process of claim 1, where the sulfonation reaction affords less than about 0.5% by weight dimer alkyl glyceryl sulfonate of formula II:

II

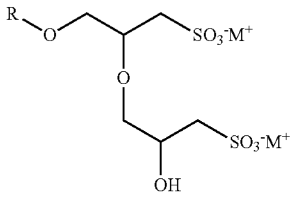

where R is a $C_{4-12}$ alkyl and M is an alkali metal.

14. The process of claim 1, where the sulfonation reaction affords about zero percent by weight trimer alkyl glyceryl sulfonate of formula III:

III

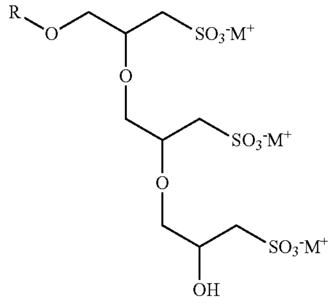

where R is a $C_{4-12}$ alkyl and M is an alkali metal.

15. The process of claim 1, further comprising processing the alkyl glyceryl sulfonate of formula I into an antimicrobial composition.

16. A process for preparing alkyl glyceryl sulfonate which comprises:

fractionally distilling an alkyl glyceryl epoxide mixture to afford alkyl glyceryl epoxide of formula IV:

IV

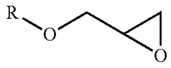

where R is a $C_{4-12}$ alkyl, in at least about 98.0% purity by weight with respect to epoxidized compounds, the epoxidized compounds comprising the alkyl glyceryl epoxide of formula IV, dimer alkyl glyceryl epoxide of formula V, and trimer alkyl glyceryl epoxide of formula VI:

V

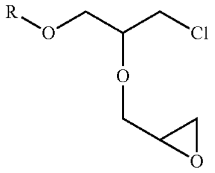

VI

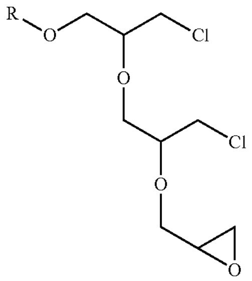

where R is a $C_{4-12}$ alkyl; and reacting the at least about 98.0% alkyl glyceryl epoxide of formula IV with a mixture of an alkali bisulfite and an alkali sulfite in a sulfonation reaction at a temperature of below about 200° C. for a time between about 30 minutes to about 165 minutes, and at a concentration of less than about 50.0% by weight alkyl glyceryl epoxide of formula IV, to afford the compound of formula I:

I

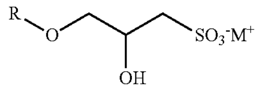

where R is a $C_{4-12}$ alkyl and M is an alkali metal.

17. The process of claim 16, where the temperature of the sulfonation reaction is about 185° C. to about 190° C. for a time between about 120 minutes to about 160 minutes, and where the concentration of the alkyl glyceryl epoxide of formula IV is about 30% to about 40% by weight.

18. A process for preparing alkyl glyceryl sulfonate which comprises:

fractionally distilling an alkyl glyceryl epoxide mixture to afford alkyl glyceryl epoxide of formula IV:

IV

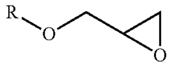

where R is a $C_{4-12}$ alkyl, in at least about 98.0% purity by weight with respect to epoxidized compounds, the epoxidized compounds comprising the alkyl glyceryl epoxide of formula IV, dimer alkyl glyceryl epoxide of formula V, and trimer alkyl glyceryl epoxide of formula VI:

V

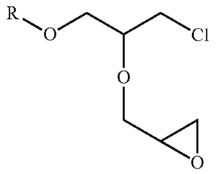

VI

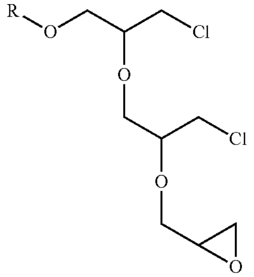

where R is a $C_{4-12}$ alkyl; and reacting the at least about 98.0% alkyl glyceryl epoxide of formula IV with a mixture of an alkali bisulfite and an alkali sulfite in a sulfonation reaction at a pressure between about 115 PSIG and about 135 PSIG, and at a concentration of about 15% to about 25% by weight alkyl glyceryl epoxide of formula IV, to afford the compound of formula I:

I

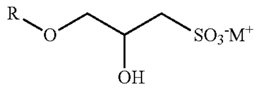

where R is a $C_{4-12}$ alkyl and M is an alkali metal.

19. The process of claim 18, where the percentage of the dimer alkyl glyceryl epoxide of formula V after the fractional distillation step is at or below about 0.36% by weight.

20. The process of claim 18, where the percentage of the trimer alkyl glyceryl epoxide of formula VI after the fractional distillation step is about zero by weight.

21. The process of claim 18, where reacting the at least about 98.0% alkyl glyceryl epoxide of formula IV with alkali sulfite and alkali bisulfite occurs in a stainless steel reactor.

22. The process of claim 21, where the stainless steel reactor is passivated with an acid prior to the reacting step.

23. The process of claim 22, where the acid is nitric acid.

24. The process of claim 18, where the pressure is about 130 PSIG.

25. The process of claim 18, where the pH of the sulfonation reaction is about 3 to about 6.

26. The process of claim 18, where the sulfonation reaction affords less than about 0.5% by weight dimer alkyl glyceryl sulfonate of formula II:

II

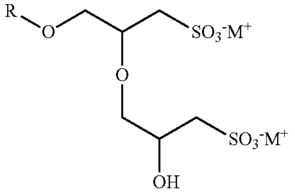

where R is a $C_{4-12}$ alkyl and M is an alkali metal.

27. The process of claim 18, where the sulfonation reaction affords about zero percent by weight trimer alkyl glyceryl sulfonate of formula III:

III

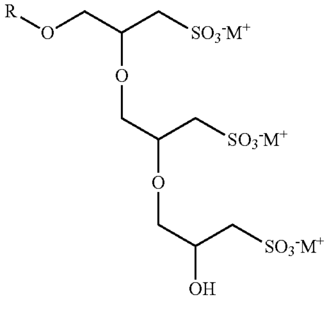

where R is a $C_{4-12}$ alkyl and M is an alkali metal.

28. The process of claim 18, further comprising processing the alkyl glyceryl sulfonate of formula I into an antimicrobial composition.

* * * * *

UNITED STATES PATENT AND TRADEMARK OFFICE

CERTIFICATE OF CORRECTION

PATENT NO. : 8,053,596 B2
APPLICATION NO. : 12/610833
DATED : November 8, 2011
INVENTOR(S) : Dennis Neigel et al.

It is certified that error appears in the above-identified patent and that said Letters Patent is hereby corrected as shown below:

On the Title Page

Left column, item (54), after "FOR PRODUCING" replace "ALXYL" with --ALKYL--.

In the Specification

In column 1, in the title, after "FOR PRODUCING" replace "ALXYL" with --ALKYL--.

Signed and Sealed this
Twenty-seventh Day of March, 2012

David J. Kappos
*Director of the United States Patent and Trademark Office*